(12) United States Patent
Bingham et al.

(10) Patent No.: US 7,340,349 B2
(45) Date of Patent: Mar. 4, 2008

(54) METHOD AND SYSTEM FOR IDENTIFYING SPLICE VARIANTS OF A GENE

(76) Inventors: Jonathan Bingham, 615 Cole St., #4, San Francisco, CA (US) 94117; Subha Srinivasan, 20 Corte Patencio, Greenbrae, CA (US) 94904

( * ) Notice: Subject to any disclaimer, the term of this patent is extended or adjusted under 35 U.S.C. 154(b) by 137 days.

(21) Appl. No.: 10/146,720

(22) Filed: May 14, 2002

(65) Prior Publication Data

US 2003/0087261 A1    May 8, 2003

Related U.S. Application Data

(60) Provisional application No. 60/343,298, filed on Dec. 21, 2001, provisional application No. 60/343,286, filed on Dec. 21, 2001, provisional application No. 60/343,269, filed on Dec. 21, 2001, provisional application No. 60/329,914, filed on Oct. 17, 2001, provisional application No. 60/307,911, filed on Jul. 25, 2001.

(51) Int. Cl.
*G01N 33/48* (2006.01)
*G06G 7/48* (2006.01)
*G06F 7/00* (2006.01)

(52) U.S. Cl. ............................ 702/19; 702/20; 703/11; 707/102; 435/6; 536/24.3

(58) Field of Classification Search ............ 702/19–29; 707/102; 703/11; 536/23.1, 24.5; 435/6
See application file for complete search history.

(56) References Cited

U.S. PATENT DOCUMENTS

| | | | |
|---|---|---|---|
| 5,057,410 A | 10/1991 | Kawasaki et al. | |
| 6,001,567 A | 12/1999 | Brow et al. | |
| 6,007,231 A * | 12/1999 | Vijg et al. | 702/20 |
| 6,100,030 A | 8/2000 | McCasky Feazel et al. | |
| 6,171,793 B1 | 1/2001 | Phillips et al. | |
| 6,210,892 B1 | 4/2001 | Bennett et al. | |
| 6,303,301 B1 * | 10/2001 | Mack | 435/6 |
| 6,632,610 B2 | 10/2003 | Thill | |
| 6,713,257 B2 * | 3/2004 | Shoemaker et al. | 435/6 |
| 6,881,571 B1 | 4/2005 | Schweighoffer et al. | |
| 6,887,662 B1 | 5/2005 | Alajem et al. | |
| 2002/0048763 A1 * | 4/2002 | Penn et al. | 435/6 |
| 2002/0081590 A1 * | 6/2002 | Penn et al. | 435/6 |
| 2003/0040870 A1 | 2/2003 | Anderson et al. | |
| 2003/0097223 A1 * | 5/2003 | Nakae et al. | 702/20 |
| 2003/0219805 A1 | 11/2003 | Kelman et al. | |

FOREIGN PATENT DOCUMENTS

| | | |
|---|---|---|
| EP | 0 668 350 A1 | 8/1995 |
| WO | WO 99/46403 A1 | 9/1999 |
| WO | WO 00/47765 | 8/2000 |
| WO | WO 01/81632 A1 | 11/2001 |
| WO | WO 02/16650 A2 | 2/2002 |
| WO | WO 02/068579 A2 | 9/2002 |

OTHER PUBLICATIONS

Bioinformatics: Methods and Protocols (Misener and Krawetz EDS. Methods in Molecular Biology vol. 132, (2000) Humana Press, Totowa, NJ, Chapters 19-20, pp. 351-386.).*
Lin et al., *Neuron*, 18:153-166 (1997).
Maas et al., *Clinical Cancer Research*, 7:868-875 (2001).
Svineng et al., *Biochemical Journal*, 330:1255-1263 (1998).
Virts et al., *Molecular Immunology*, 35:167-176 (1998).
Williams et al., *Analytical Biochemistry*, 271:194-197 (1999).
Adams, M.D., et al., *Science*, 252:1651-1656, (1991).
Black, D.L., *Cell*, 103:367-370, (2000).
Brown, P.O. and Botstein, D., *Nature Genetics Supplement*, 21:33-37, (1999).
Burge, C. and Karlin, S., *J. Mol. Biol.*, 268(1):78-94, (1997).
Hanke, J., et al., *Trends in Genetics*, 15(10):389-390, (1999).
Hu, G.K., et al., *Genome Research*, 11:1237-1245, (2001).
Kan, Z., et al., *Genome Research*, 11:889-900, (2001).
Lander, E.S., et al., *Nature*, 409:860-921, (2001).
Shoemaker, D.D., et al., *Nature*, 409:922-926, (2001).
Sorek, R. and Amitai, M., *Nature Biotechnology*, 19:196, (2001).

* cited by examiner

*Primary Examiner*—Mary K. Zeman
(74) *Attorney, Agent, or Firm*—Perkins Coie LLP

(57) ABSTRACT

A method and system for identifying mRNA present in a sample. A splice variant technique selects a set of possible exon-exon junctions based on exons of expected mRNA transcripts. The splice variant technique then selects indicator polynucleotides for the exon-exon junctions and detects the expression level of the indicator polynucleotides in the sample. The splice variant technique then may use a mathematical algorithm to identify possible splice variants in the sample from the observed expression levels.

3 Claims, 4 Drawing Sheets

METHOD AND SYSTEM FOR IDENTIFYING SPLICE VARIANTS OF A GENE

CROSS-REFERENCE TO RELATED APPLICATION(S)

This application claims the benefit of U.S. Provisional Application No. 60/307,911 filed on Jul. 25, 2001, U.S. Provisional Application No. 60/329,914 filed on Oct. 17, 2001, U.S. Provisional Application No. 60/343,298 filed on Dec. 21, 2001, U.S. Provisional Application No. 60/343,286 filed on Dec. 21, 2001 and U.S. Provisional Application No. 60/343,269 filed on Dec. 21, 2001 which are hereby incorporated by reference in their entirety.

TECHNICAL FIELD

The described technology relates generally to identifying splice variants.

BACKGROUND

A splice variant of a gene results from a selective transcription of the exons of the gene. Each multi-exon gene has a transcription start site (i.e., TATA box), promoter elements, exons and introns, and a transcription end site (i.e., a poly-adenylation site). The splicing machinery removes introns and splices adjacent exons together to form mRNA. The promoter elements regulate the removal of introns and splicing of adjacent exons in a way that is tissue specific. The mRNA may then be translated into active or inactive proteins. FIG. 1 is a block diagram illustrating the transcription of a gene into mRNA. In this example, gene 101 includes exons 1-5 and introns 1-4. (The pre-mRNA phase of transcription is not depicted in FIG. 1.) The mRNA 102 illustrates a splice variant that is specific to brain tissue. The mRNA 102 includes exons 1-5. The transcription start site is the TATA box, and transcription end site is the poly-A tail. The mRNA 102 includes four exon-exon junctions, that is the junctions between exon 1 and exon 2, exon 2 and exon 3, exon 3 and exon 4, and exon 4 and exon 5. The mRNA 103 illustrates a splice variant that is specific to heart tissue. The mRNA 103 includes exon 1, exon 2, exon 4, and exon 5. Exon 3 was omitted during the transcription process; it is thus an optional exon in the splice variants. The mRNA 103 includes three exon-exon junctions that is, the junctions between exon 1 and exon 2, exon 2 and exon 4, and exon 4 and exon 5.

It is generally considered that the complexity of higher organisms is achieved by the diversity of expressed proteins, which are regulated by the alternate splicing of genes. Alternate splicing increases the protein diversity by allowing multiple, sometimes functionally distinct, proteins to be encoded in the same gene. The variants of a given gene can be specific to tissue and to developmental and pathological states. Splice variants that result in inactive proteins and pathological conditions may provide useful links between genotypes and the corresponding phenotypes leading to their functions. Thus, it would be desirable to decipher all possible splice variants of a gene along with their expression/tissue specificity.

DETAILED DESCRIPTION

Figure 1:
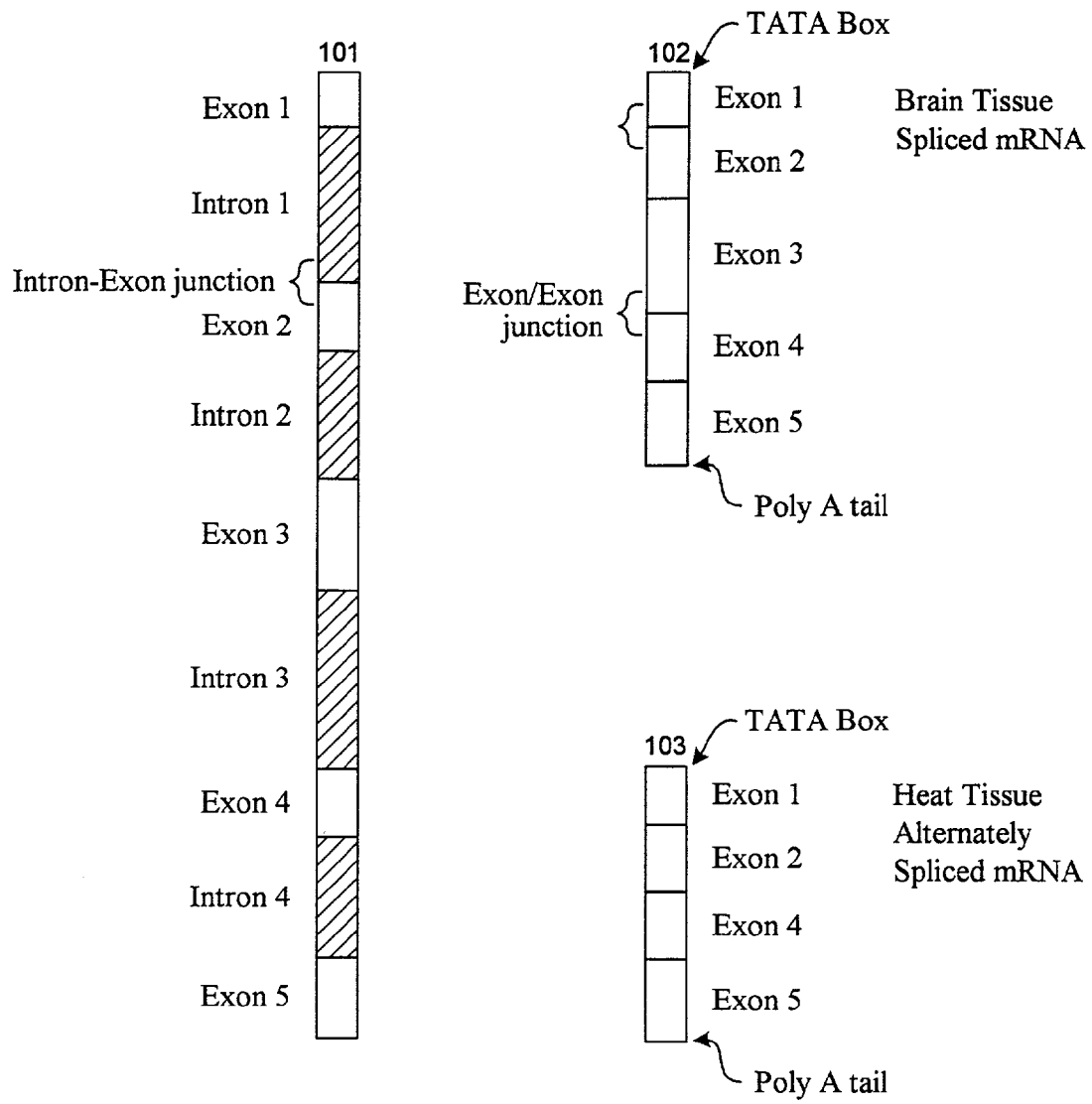
FIG. 1 is a block diagram illustrating the transcription of a gene into mRNA.

A method and system for identifying mRNA present in a sample is provided. Exemplary samples may be a tissue sample, total RNA, a cell line, a biological sample containing polynucleotides, a polynucleotide probe, and so on. In one embodiment, the splice variant technique selects a set of possible exon-exon junctions based on exons of expected (i.e., known or predicted) mRNA transcripts. The splice variant technique may select all possible exon-exon junctions. The splice variant technique then selects indicator polynucleotides whose presence in the sample indicates the presence of an exon-exon junction that is in the set. The splice variant techniques design probes to detect or observe the expression level of the indicator polynucleotides in the sample using nucleotide array technology. The expression levels of the indicator polynucleotides indicate the expression levels of the exon-exon junctions. An indicator polynucleotide may be a portion of (or all of) a polynucleotide whose presence indicates the presence of the polynucleotide itself. For example, the indicator polynucleotide for an exon-exon junction includes nucleotides from both exons and may include a polynucleotide starting at the 3' end of the upstream exon and a polynucleotide starting at the 5' end of the downstream exon. Alternatively, an indicator polynucleotide may be a polynucleotide complementary to a portion (or all of) a polynucleotide whose presence indicates the presence of the polynucleotide itself. The splice variant technique uses a mathematical algorithm to identify possible splice variants in the sample from the observed expression levels. The mathematical algorithm may be an algorithm for solving linear equations, a least squares algorithm, or any other algorithm for finding a possible solution for a set of equations. The splice variant technique may also detect the expression levels of the exons themselves to provide more information for use in identifying the splice variants in the sample. The splice variant technique detects the expression levels of the exons by selecting indicator polynucleotides for the exons and designing probes to detect the expression level of the indicator polynucleotides (and thus the exons themselves) in the sample using the nucleotide array technology.

In an alternate embodiment, the splice variant technique identifies splice sites within a sample. The splice variant technique selects a set of polynucleotides that are in expected mRNA transcripts. The set of polynucleotides includes exons and exon-exon junctions. The splice variant technique selects indicator polynucleotides to detect the expression levels of the exons and exon-exon junctions in the sample using nucleotide array technology. If the splice variant technique detects the presence of both exons of an exon-exon junction, but not the junction itself, then the splice variant technique uses polymerase chain reaction ("PCR") technology to identify the polynucleotide that spans the exons. The splice variant technique may clone the PCR product to identify the spanning polynucleotide. Alternatively, the splice variant technique may identify the spanning polynucleotide by comparing the molecular weight of the PCR product to the molecular weights of predicted spanning polynucleotides identified in genomic DNA. Once the spanning polynucleotide is identified, it may be combined with knowledge of other expected mRNA transcripts to identify additional splice variants and splice sites. The splice variant technique may identify subsets of the sequences of exons in a sample. For example, the splice variant technique may identify full-length splice variants (e.g., a complete mRNA from TATA box to poly-A tail) or sequences that span a complete coding region for a protein (e.g., initiating methianine to stop codon).

In one embodiment, the splice variant technique selects exons and exon-exon junctions based on known or predicted mRNA transcripts. The splice variant technique may identify exon-intron junctions from a known database of cDNA. The splice variant techniques searches (e.g., using a BLAST algorithm or a Smith-Waterman algorithm) the cDNA sequences against the BAC sequences. The start and end base numbers for both the cDNA and the BAC sequences are determined for each block of matching polynucleotides. Each block, however, may not mark the exact exon-intron junction because of spurious matches that often extend beyond the exon-intron boundaries. The splice variant technique may remove the spurious matches by removing or extending bases for both ends of the polynucleotide corresponding to each block until an intron end signature (e.g., GT) is removed from the 5' end and an intron start signature (e.g., AG) is removed from the 3' end. Any scoring mechanism, such as a weight matrix or Markov Model, can be used to select the best boundary for the exon-intron junction. By matching the translated sequence to the corresponding protein sequence, the splice variant technique may further validate the integrity of the splice junction.

The splice variant technique may limit the number of possible exon-exon junctions by using only in-frame variants of the gene. An exon can have three phases at each end corresponding to (1) no extra bases, (2) one extra base, or (3) two extra bases. To ensure that only in-frame variants are used, the splice variant technique selects exon-exon junctions for only those pairs of exons whose extra bases at the 3' end of the upstream exon and extra bases at the 5' end of the downstream exon result in the coding of a complete triplet for an amino acid. In particular, an exon with no extra bases on its 3' end would be matched with only those exons with no extra bases on its 5' end, an exon with one extra base on its 3' end would be matched with only those exons with two extra bases on its 5' end, and an exon with two extra bases on its 3' end would be matched only with those exons with one extra base on its 5' end.

The splice variant technique then selects indicator polynucleotides for the exons and the exon-exon junctions and designs probes for use with the nucleotide array technology. Since all possible in-frame, exon-exon junctions may be used with the nucleotide array technology, the splice variant technique generates an extensive map of the variants present in the sample. The following illustrates the splice variant technique for identifying splice variants in a sample. Table 1 lists the seven expected exons of the sample along with their phases. The phase of the 3' end of exon 2 is one, and the phase at the 5' end of exon 4 is two. Since the sum of their phases is three, the exon-exon junction of exon 2 and exon 4 (J2-4) is a possible in-frame variant.

TABLE 1

| Exon | 5' | 3' |
|------|----|----|
| 1 | — | 0 |
| 2 | 0 | 1 |
| 3 | 2 | 1 |
| 4 | 2 | 0 |
| 5 | 0 | 0 |
| 6 | 0 | 0 |
| 7 | 0 | — |

Table 2 lists all the possible in-frame variants for these seven exons. Each row lists a possible variation of in-frame, exon-exon junctions. For example, variant "V7" indicated that a possible in-frame variant comprises exons 1, 2, 4, 5, and 7. However, a variant comprising exons 1, 2, 5, and 7 is not a possible in-frame variant because the phase of the 3' end of exon 2 and the phase of the 5' end of exon 5 do not code an integral amino acid.

TABLE 2

| Variant | Variants | | | | | | |
|---------|---|---|---|---|---|---|---|
| V1  | 1 | 2 | 3 | 4 | 5 | 6 | 7 |
| V2  | 1 | 2 | 3 | 4 | 5 |   | 7 |
| V3  | 1 | 2 | 3 | 4 |   | 6 | 7 |
| V4  | 1 | 2 |   | 4 |   |   | 7 |
| V5  | 1 | 2 |   | 4 | 5 | 6 | 7 |
| V6  | 1 | 2 |   | 4 |   | 6 | 7 |
| V7  | 1 | 2 |   | 4 | 5 |   | 7 |
| V8  | 1 | 2 | 3 | 4 |   |   | 7 |
| V9  | 1 |   |   |   |   | 6 | 7 |
| V10 | 1 |   |   |   | 5 | 6 | 7 |
| V11 | 1 |   |   |   |   |   | 7 |

Table 3 illustrates sample results from the nucleotide array technology. Each row corresponds to a variant, and each column corresponds to a possible exon-exon junction. Each cell indicates whether that exon-exon junction is in that variant. The bottom row indicates the observed expression levels of the exon-exon junctions as indicated by the intensity values of the nucleotide array. For example, variant "V7" includes exon-exon junctions J1-2, J2-4, J4-5, and J5-7. The expression level for exon-exon junction J1-2 is "a," J2-4 is "h," J4-5 is "d," and J5-7 is "k," as indicated by the bottom row. The exon-exon junctions that are not in-frame, such as exon-exon junction J1-3, may have no expression level.

TABLE 3

| | Exon–exon junction | | | | | | | | | | | | | | | | | | | | |
|---------|----|----|----|----|----|----|----|----|----|----|----|----|----|----|----|----|----|----|----|----|----|
| Variant | 12 | 23 | 34 | 45 | 56 | 67 | 13 | 24 | 35 | 46 | 57 | 14 | 25 | 36 | 47 | 15 | 26 | 37 | 16 | 27 | 17 |
| V1 | Y | Y | Y | Y | Y | Y | | | | | | | | | | | | | | | |
| V2 | Y | Y | Y | Y | | | | | | | Y | | | | | | | | | | |
| V3 | Y | Y | Y | | | | | Y | | | | | | Y | | | | | | | |
| V4 | Y | | | | | | | Y | | | | | | | Y | | | | | | |

TABLE 3-continued

| | Exon–exon junction | | | | | | | | | | | | | | | | | | | | |
|---|---|---|---|---|---|---|---|---|---|---|---|---|---|---|---|---|---|---|---|---|---|
| Variant | 12 | 23 | 34 | 45 | 56 | 67 | 13 | 24 | 35 | 46 | 57 | 14 | 25 | 36 | 47 | 15 | 26 | 37 | 16 | 27 | 17 |
| V5 | Y | | | Y | Y | Y | | Y | | | | | | | | | | | | | |
| V6 | Y | | | | Y | | | Y | Y | | | | | | | | | | | | |
| V7 | Y | | Y | | | | | Y | | Y | | | | | | | | | | | |
| V8 | Y | Y | Y | | | | | | | | | | | | | Y | | | | | |
| V9 | | | | | | | | Y | | | | | | | | | Y | | | | |
| V10 | | | Y | Y | | | | | | | | | | | | Y | | | | | |
| V11 | | | | | | | | | | | | | | | | | | | | | Y |
| | a | b | c | d | e | f | g | h | i | j | k | l | m | n | o | p | q | r | s | t | u |

Table 4 illustrates equations used in calculating the relative amount of each variant in the sample. These 21 equations are derived from Table 3. For example, equation 5 indicates that the sum of relative expression levels of variants V1, V5, and V10 is "e." Since there are 13 equations and 11 variables, the equations are over-specified and a unique solution can be found for the relative expression levels for each of the 11 variants.

TABLE 4

| | | |
|---|---|---|
| 1. | V1 + V2 + V3 + V4 + V5 + V6 + V7 = | a |
| 2. | V1 + V2 + V3 + V8 = | b |
| 3. | V1 + V2 + V3 + V8 = | c |
| 4. | V1 + V2 + V5 + V7 = | d |
| 5. | V1 + V5 + V10 = | e |
| 6. | V1 + V3 + v5 + V6 + V9 + V10 = | f |
| 7. | | |
| 8. | V4 + v5 + v6 + v7 = | h |
| 9. | | |
| 10. | V3 + V6 = | j |
| 11. | V2 + V7 = | k |
| 12. | | |
| 13. | | |
| 14. | | |
| 15. | V4 + V8 = | o |
| 16. | V10 = | p |
| 17. | V9 = | q |
| 18. | | |
| 19. | | |
| 20. | | |
| 21. | V11 = | u |

Figure 2:
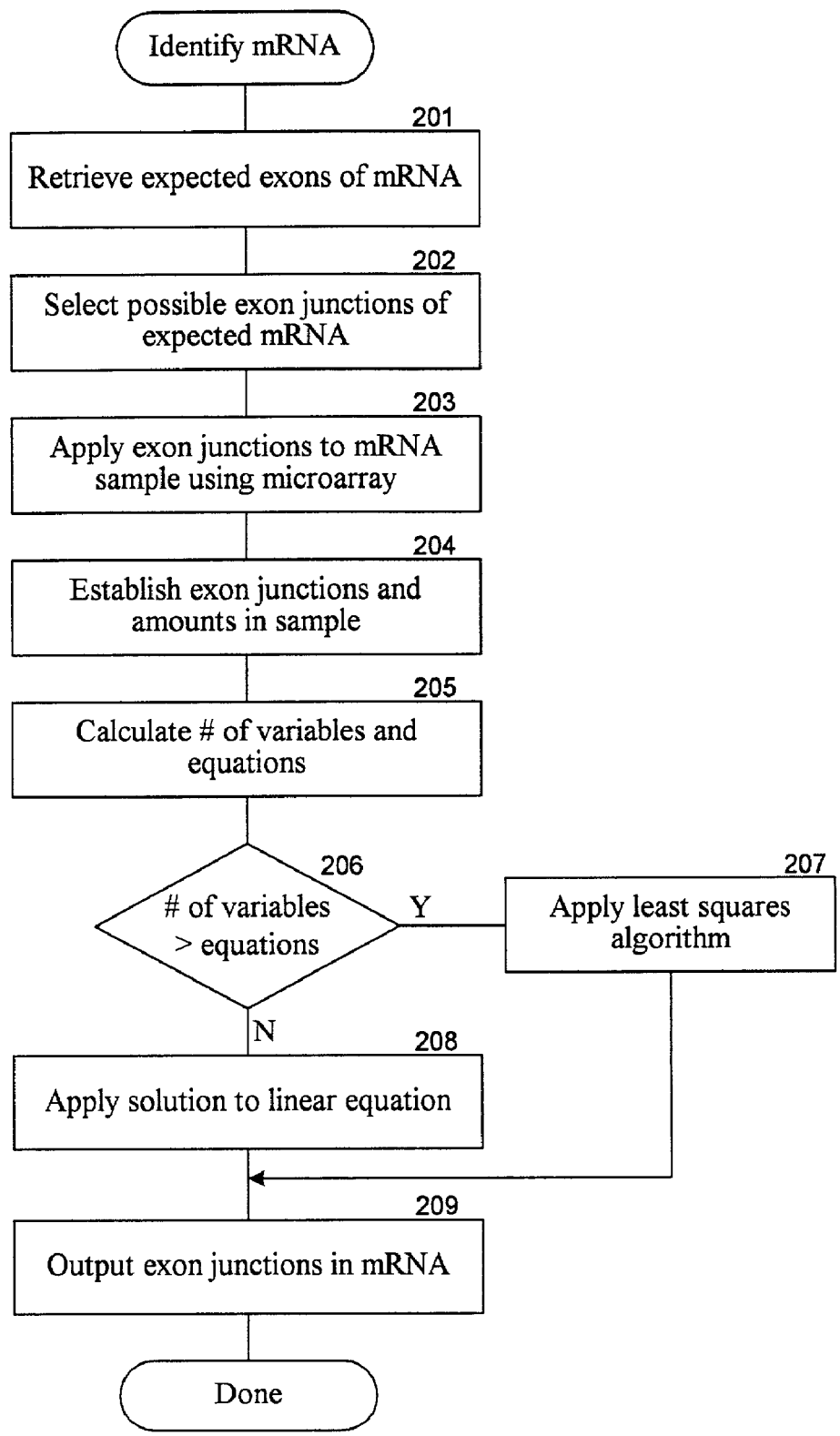
FIG. 2 is a flow diagram illustrating a process of identifying splice variants in a sample in one embodiment.

FIG. 2 is a flow diagram illustrating a process of identifying splice variants in a sample in one embodiment. In block 201, the technique retrieves the expected exons of the mRNA transcript. The expected exons may be known or predicted exons. The technique may trim and extend the exons as discussed above. In block 202, the technique selects all possible exon-exon junctions for the expected mRNA transcripts. In one embodiment, the technique selects only in-frame, exon-exon junctions. In an alternate embodiment, the technique selects only those exon-exon junctions of an expected mRNA transcript. In block 203, the technique selects indicator polynucleotides for the selected exon-exon junctions, designs probes for the indicator polynucleotides, and applies the probes to the sample using nucleotide array technology. In block 204, the technique retrieves the resulting observed expression level for each exon-exon junction. One skilled in the art will appreciate that various methods of identifying expression levels from the nucleotide array data may be used, such as subtracting a background expression level, performing algorithmic transformation of the expression levels, or scaling the expression levels according to a set of internal controls. In block 205, the technique calculates the number of variables (e.g., corresponding to the number of possible variants) and the number of expression levels for the detected exon-exon junctions. In decision block 206, if the number of variables is greater than the number of expression levels, then there is not a unique solution and the technique continues at block 207, else the solution is unique and the technique continues at block 208. In block 207, the technique applies a mathematical algorithm (e.g., a least-squares algorithm) to estimate the relative amounts of each variant. In block 208, the technique solves linear equations representing the possible variants that contribute to the expression level of each exon-exon junction. In block 209, the technique outputs the calculated relative amount of each variant in the sample. One skilled in the art will appreciate that in addition to the exon-exon junction-specific probes, one may apply exon-specific probes using the nucleotide array technology. In such a case, the additional information may be sufficient to provide a unique solution to the linear equations. In addition, one skilled in the art will appreciate that various algorithms may be used to predict the expression level of each variant based on the overall accuracy of detecting expression levels using the nucleotide array technology.

In an alternate embodiment, the splice variant technique identifies novel exons or exons with alternate boundaries using the expression levels of exons and exon-exon junctions. For example, if probes corresponding to exons 1 and 2 hybridize without a probe corresponding to their junction hybridizing, then it can be inferred that an extra exon, a 3' extension or trim of exon 1, or a 5' extension or trim of exon 2 is present. The splice variant technique may use PCR technology to identify possible exons or exon extensions/trims between exons 1 and 2 and to identify the polynucleotides of novel exons and alternately bounded exons. As discussed above, the polynucleotide can be identified by cloning the PCR product or by comparing the molecular weight of the polynucleotide to predicted polynucleotides. These new exons or extension/trims can be iteratively added to the list of expected exons to design more in-frame variants for that gene.

Figure 3:
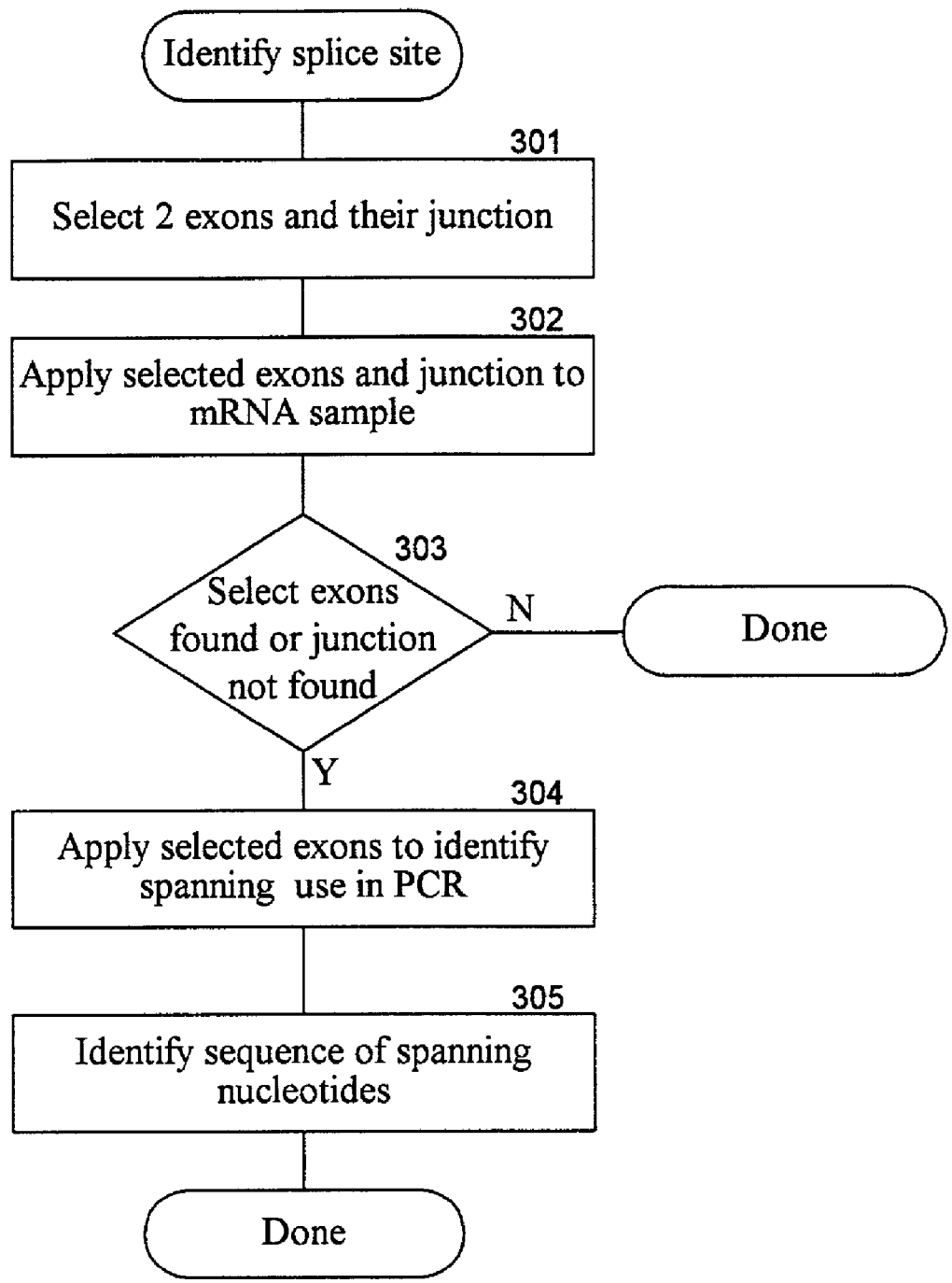
FIG. 3 is a flow diagram illustrating a process of identifying alternate splice sites in one embodiment.

FIG. 3 is a flow diagram illustrating a process of identifying alternate splice sites in one embodiment. In block 301, the technique selects a pair of exons and their exon-exon junction. In block 302, the technique selects indicator polynucleotides, designs probes, and applies the probes for the selected exons and their exon-exon junction to the sample using nucleotide array technology. In decision block 303, if the selected exons are found in the sample, but their exon-exon junction is not found (or the expression levels indicate that these exons are not adjacent in all the mRNA in the sample), then there is an alternate splice variation between the selected exons and the technique continues at block 304, else the technique completes. In block 304, the technique applies the selected exons to isolate the polynucleotide that spans exons 1 and 2 using PCR technology. In block 305, the technique identifies nucleotides in the spanning polynucleotide using PCR cloning or known molecular weights. The technique then completes.

Figure 4:
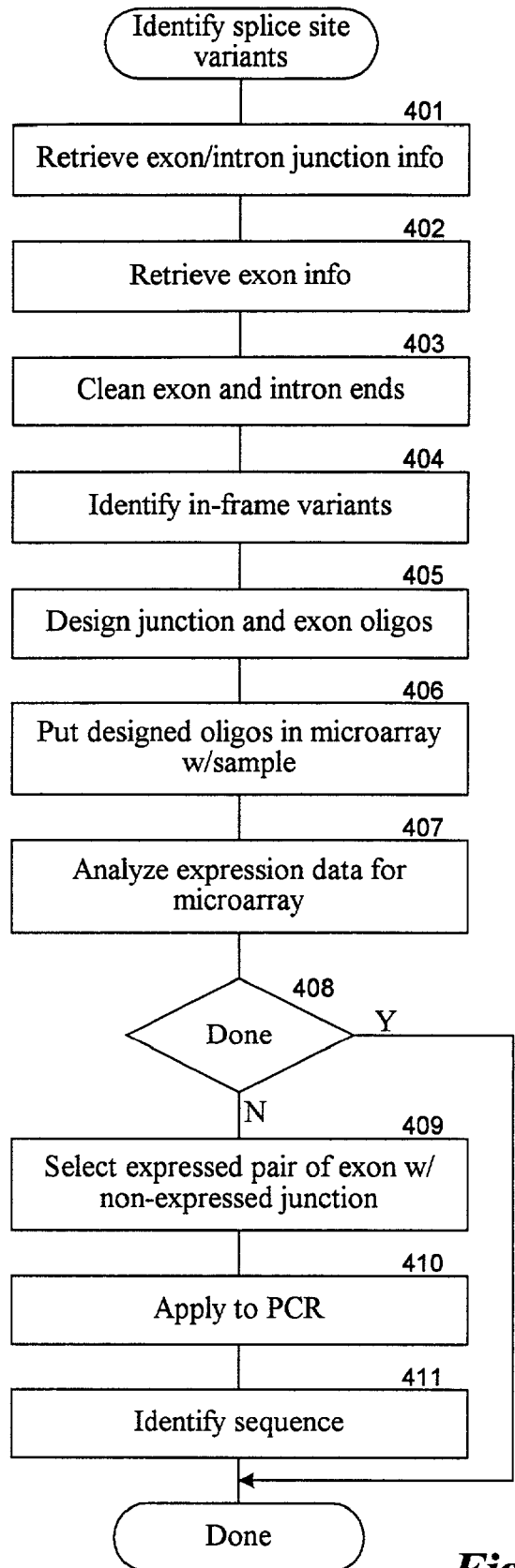
FIG. 4 is a flow diagram illustrating more detailed processing of identifying splice site variants in one embodiment.

FIG. 4 is a flow diagram illustrating more detailed processing of identifying splice site variants in one embodiment. In block 401, the technique retrieves information describing the exon/intron junctions from, for example, well-known databases. In block 402, the function retrieves exon information from well-known databases. In block 403, the technique cleans (e.g., removes spurious matches) the exon and intron ends. In block 404, that technique identifies all in-frame, exon-exon junctions. In block 405, the technique selects indicator polynucleotides for the exons and the exon-exon junctions and designs probes to hybridize with the indicator polynucleotides. In block 406, the component applies the probes to a sample using nucleotide array technology. In block 407, the technique analyzes the resulting expression data from the nucleotide array. In decision block 408, if the analysis indicates that there are no new variants, then the technique completes, else the technique continues at block 409. In block 409, the technique selects a pair of exons that were both expressed using the nucleotide array technology but whose exon-exon junction was not expressed or not sufficiently expressed to account for the expression levels of the pair of exons. In block 410, the technique applies the selected exons to the sample using PCR technology. In block 411, the technique identifies the spanning polynucleotide using PCR cloning or known molecular weights and then completes.

In the following, three examples using the splice variant techniques are provided. In the first example, the sample contains a single splice variant. The splice variant technique identifies that splice variant by determining the expression level for the exons and exon-exon junctions using nucleotide array technology and solving the resultant linear equations. In the example, the gene has four exons (E1, E2, E3, and E4), and all six exon-exon junctions (J1-2, J1-3, J1-4, J2-3, J2-4, and J3-4) are in-frame. The possible splice variants are:

V1-2
V1-2-3
V1-2-3-4
V1-3
V1-3-4
V1-4
V2-3
V2-3-4
V2-4
V3-4

The splice variant technique in this example selects indicator polynucleotides and designs probes for all four exons and all six exon-exon junctions to maximize the expression level information gained as a result of the hybridization using nucleotide array technology. The results of the hybridization indicate that E1, E3, E4, J1-3, and J3-4 are the only probes that hybridized and that they all have approximately the same expression level.

Analysis of the results indicates that all splice variants with exon E2 can be eliminated because exon E2 was not expressed and that splice variant V1-4 can be eliminated because J1-4 was not expressed. This leaves splice variants V1-3, V1-3-4, and V3-4 as possible splice variants in the sample. However, since the probes that hybridized were at approximately the same expression level, splice variants V1-3 and V3-4 can be eliminated because any combination of these two junctions would necessarily result in an expression level for exon E3 that is higher than the expression levels for exons E1 and E4. The expression levels for exons E1, E3, and E4 can only be equal if they are all in the same splice variant. Thus, the unique solution is splice variant V1-3-4.

The solution can be written in the form of simultaneous linear equations (as can the solution for arbitrarily complex examples with any number of exons, with or without partial codons at either end). H(En) is the expression value measured for exon n, H(Jn) is the expression value measured for junction n, and H(Vn) is the expression value to be calculated for splice variant n. Since exon E3 can be expressed in splice variants V1-3, V3-4, and V1-3-4, the expression level for exon E3 is the sum of the expression levels for splice variants V1-3, V3-4 and V1-3-4 as indicated by the equations below. Also, since junction J1-3 can only be expressed in splice variants V1-3 and V1-3-4, the expression level for junction J1-3 is the sum of the expression levels for splice variants V1-3 and V1-3-4 as indicated by the equations below. The expression levels for the unexpressed exons and exon-exon junctions of E2, J1-2, J1-4, J2-3, and J2-4 are set to zero.

$$H(E1)=H(V1\text{-}3)+H(V1\text{-}3\text{-}4)$$

$$H(E2)=0$$

$$H(E3)=H(V1\text{-}3)+H(V3\text{-}4)+H(V1\text{-}3\text{-}4)$$

$$H(E4)=H(V3\text{-}4)+H(V1\text{-}3\text{-}4)$$

$$H(J1\text{-}2)=0$$

$$H(J1\text{-}3)=H(V1\text{-}3)+H(V1\text{-}3\text{-}4)$$

$$H(J1\text{-}4)=0$$

$$H(J2\text{-}3)=0$$

$$H(J2\text{-}4)=0$$

$$H(J3\text{-}4)=H(V3\text{-}4)+H(V1\text{-}3\text{-}4)$$

Since each of the observed expression levels are approximately the same, the equations can be simplified to the following, where H is the expression level.

$$H=H(V1\text{-}3)+H(V1\text{-}3\text{-}4)$$

$$H=H(V1\text{-}3)+H(V3\text{-}4)+H(V1\text{-}3\text{-}4)$$

$$H=H(V3\text{-}4)+H(V1\text{-}3\text{-}4)$$

$$H=H(V1\text{-}3)+H(V1\text{-}3\text{-}4)$$

$$H=H(V3\text{-}4)+H(V1\text{-}3\text{-}4)$$

Since these are 3 variables and 5 equations a unique solution exists. The unique solution to these simultaneous linear equations is that H(V1-3)=0, H(V3-4)=0, and H(V1-3-4)=H, which indicates that only splice variant V1-3-4 is present in the sample.

In the second example, the sample contains multiple splice variants. This example is the same as above except that the observed expression levels are $$H(E1)=H(E4)=2*H(E2)=2*H(E3)=2*H(J2\text{-}4)=2*H(J1\text{-}3)=2*H(J1\text{-}2)=2*H(J3\text{-}4)$$

The following is a list of the linear equations that reflect the non-expression of junctions J1-4 and J2-3 in the sample.

$$H(E1)=H(V1\text{-}2)+H(V1\text{-}3)+H(V1\text{-}2\text{-}4)+H(V1\text{-}3\text{-}4)$$

$H(E2)=H(V1\text{-}2)+H(V2\text{-}4)+H(V1\text{-}2\text{-}4)$ $H(E3)=H(V1\text{-}3)+H(V3\text{-}4)+H(V1\text{-}3\text{-}4)$ $H(E4)=H(V2\text{-}4)+H(V3\text{-}4)+H(V1\text{-}2\text{-}4)+H(V1\text{-}3\text{-}4)$ $H(J1\text{-}2)=H(V1\text{-}2)+H(V1\text{-}2\text{-}4)$ $H(J1\text{-}3)=H(V1\text{-}3)+H(V1\text{-}3\text{-}4)$ $H(J1\text{-}4)=0$ $H(J2\text{-}3)=0$ $H(J2\text{-}4)=H(V2\text{-}4)+H(V1\text{-}2\text{-}4)$ $H(J3\text{-}4)=H(V3\text{-}4)+H(V1\text{-}3\text{-}4)$ Applying the observed expression levels to the equations results in the following equations, where H represents the expression level of exon E1.

$H=H(V1\text{-}2)+H(V1\text{-}3)+H(V1\text{-}2\text{-}4)+H(V1\text{-}3\text{-}4)$ $H=2*(H(V1\text{-}2)+H(V2\text{-}4)H(V1\text{-}2\text{-}4))$ $H=2*(H(V1\text{-}3)+H(V3\text{-}4)+H(V1\text{-}3\text{-}4))$ $H=H(V2\text{-}4)+H(V3\text{-}4)+H(V1\text{-}2\text{-}4)+H(V1\text{-}3\text{-}4)$ $H=2*(H(V1\text{-}2)+H(V1\text{-}2\text{-}4))$ $H=2*(H(V1\text{-}3)+H(V1\text{-}3\text{-}4))$ $H=2*(H(V2\text{-}4)+H(1\text{-}2\text{-}4))$ $H=2*(H(V3\text{-}4)+H(V1\text{-}3\text{-}4))$ Since there are six variables with eight equations, there is a unique solution. The solution is H(V1-2)=0, H(V1-3)=0, H(V2-4)=0, H(V3-4) =0, H(V1-2-4)=H, and H(V1-3-4)=H. Thus, splice variants V1-2-4 and V1-3-4 are the only variants of the sample and they are expressed in equal amounts.

In the third example, the sample contains a missing or alternate exon or a retained intron. This example is the same as above except that the observed expression levels are $H(E1)=H(E2)=H(E4)=H(J2\text{-}4)$ It is apparent that there is something between exons E1 and E2 because each of these exons is expressed, but their junction is not. Either exon E1 or exon
E2 is extended or trimmed or there is an additional exon or a retained intron between exons E1 and E2.

The splice variant technique uses PCR technology to isolate the polynucleotide that spans exons E1 and E2. The technique then uses PCR cloning or molecular weights to identify the spanning polynucleotide. When molecular weights are used, the technique identifies an alternate or additional exon or retained intron with a molecular weight that most closely matches the molecular weight of the spanning polynucleotide. For example, if the molecular weight of the splice variant with the spanning polynucleotide is determined to be less than the molecular weight of splice variant V1-2-4, the difference can be accounted for by a trim to E1 or E2. The splice variant technique computes the molecular weight of each predicted trim that, for example, maintains intron start/stop motifs and maintains phase. The splice variant technique then finds the alternate exon that accounts for the difference.

Alternatively, if the molecular weight of the splice variant with the spanning polynucleotide is determined to be greater than the molecular weight of V1-2-4, then the difference can be accounted for by an extension of exon E1 or E2, by a retained intron between E1 and E2, or by an additional exon located in the intronic polynucleotide between exons E1 and E2. The splice variant technique computes the molecular weight of exon extensions and potential exons in the intronic polynucleotide that, for example, maintain intron start/stop motifs and phase. The molecular weights for predicted alternate exons, hypothetical exons, and retained introns can be pre-computed and stored in a database, so that the splice variant technique can look up the values as needed.

The least-squares technique may be used when a unique solution does not exist. The technique may iterate over the following equation until the result converges on a solution (e.g., two successive iterations have solutions within a threshold distance). The equation is $S=(M*M^T)^{-1}*M^T*E$ Where S is a solution vector of coefficients for each expected mRNA transcript (e.g., splice variant).

M is a matrix with a column for each expected mRNA transcript and a row for each exon or exon-exon junction whose expression level is to be determined using the nucleotide array technology. The value of a cell of the matrix may be zero or one to indicate whether the expected mRNA transcript of that column contains the exon or exon-exon junction for that row.

E is a vector of expression values, which is initially set to the expression values resulting from the nucleotide array.

The following example using splice variant techniques is provided. The gene has four exons (E1, E2, E3, and E4) as in the example above, but only four exon-exon junctions (J1-2, J1-3, J2-4, and J3-4) are in-frame. The expected splice variants are

V1-2

V1-3

V1-2-4

V1-3-4.

Since there are four splice variants matrix M has four columns. If eight indicator polynucleotides (one for each exon and in-frame junction) are used, then matrix M has eight rows.

$$M = \begin{array}{c|cccc|c} & V1\text{-}2 & V1\text{-}3 & V1\text{-}2\text{-}4 & V1\text{-}3\text{-}4 & \\ & 1 & 1 & 1 & 1 & E1 \\ & 1 & 0 & 1 & 0 & E2 \\ & 0 & 1 & 0 & 1 & E3 \\ & 0 & 0 & 1 & 1 & E4 \\ & 1 & 0 & 1 & 0 & J1\text{-}2 \\ & 0 & 1 & 0 & 1 & J1\text{-}3 \\ & 0 & 0 & 1 & 0 & J2\text{-}4 \\ & 0 & 0 & 0 & 1 & J3\text{-}4 \end{array}$$

Each row indicates whether the corresponding exon or exon-exon junction for that row is present in the corresponding splice variant for each column. For example, since the exon-exon junction J1-2 is in splice variants V1-2 and V1-2-4, but not in splice variants V1-3-4, the content of the row for exon-exon junction J1-2 is "1010," where "1" indicates presence of the exon-exon junction in a splice variant.

In this example, the observed expression values for the eight indicates polynucleotides are $$E = \begin{vmatrix} 8 & E1 \\ 4 & E2 \\ 4 & E3 \\ 8 & E4 \\ 4 & J1\text{-}2 \\ 4 & J1\text{-}3 \\ 4 & J2\text{-}4 \\ 4 & J3\text{-}4 \end{vmatrix}$$

For example, exon E1 has an expression level of 8, and exon-exon junction J1-2 had an expression level of 4. These correspond to example expression levels for the second example above.

When the least squares analysis is performed, the solution converges to $$S = \begin{vmatrix} 0 & V1\text{-}2 \\ 0 & V1\text{-}3 \\ 4 & V1\text{-}2\text{-}4 \\ 4 & V1\text{-}3\text{-}4 \end{vmatrix}$$

The solution indicates the presence of splice variants V1-2-4 and V1-3-4 in equal quantities and the absence of splice variants V1-2 and V1-3 in the sample.

In one embodiment, the iterating over the equation involves initially solving the equation to identify an initial splice variant solution S. Each iteration uses the solution S generated by the previous iteration (with the first iteration using the initial solution S). Each iteration proceeds by predicting expression levels vector E' by multiplying the matrix M by the solution S. The iteration then calculates the difference vector ΔE between the observed expression levels vector E and the predicted expression levels vector E'. The iteration then solves the equation using vector ΔE resulting in a correction solution S'. The iteration then adds the correction solution S' to splice variant solution S. This new splice variant solution S is input to the next iteration. The iterations are repeated until a termination condition is met (e.g., number of iterations or correction solution S' is less than a threshold level). The following pseudo code illustrates the iterations A=(M*M$^T$)$^{-1}$*M$^T$
S=A*E
for i=1, n
E'=M*S
ΔE=E−E'
S'=A*ΔE
S=S+S'

One skilled in the art will appreciate that many different implementions of a least squares algorithms may be used. Also, one skilled in the art will appreciate that solutions for multiple sets of observed expression levels may be solved simultaneously. For example, the expression levels may be from samples of a healthy lung, a cancerous lung, or brain tissue. In such a case the vector E would be replaced by a matrix E with one column for each set of observed expression levels. The resulting solution S would also be a matrix.

In one embodiment, the values of matrix M might be any real number (e.g., 1.1, 400, 0.25, and −2.1). Fractional values, such as values between 0 and 1, can be used to represent situations when the expected mRNA transcript contains a near, but not exact, match of an exon or an exon-exon junction. An indicator polynucleotide may find near matches in addition to exact matches. For example, an mRNA transcript containing junction J1-3 may have a near match to junctions J1-2 and J2-3. The near match can be represented as a fractional value such as 0.3. The expression level of a near match will be weaker than an exact match and certain experimental parameters, such as hybridization and wash temperatures, can be used to determine what should be counted as a near match. Non-binary values may also be used to account for expected variations in the detection sensitivity of indicator polynucleotides as a result of such factors as 3' bias in mRNA preparation (using smaller values for indicator polynucleotides closer to the 5' end and larger values near the 3' end), variations in the indicator polynucleotide melting temperatures (using smaller or larger values for each indicator polynucleotide according to its expected melting temperature), the presence of likely homologues (using larger values to account for the presence of expected homologues), and low sequence complexity (again using larger values). One skilled in the arts will appreciate the various factors that may influence the sensitivity of indicator polynucleotides as well as the ways in which the matrix values may be scaled accordingly.

From the above description, it will be appreciated that although specific embodiments of the invention have been described for purposes of illustration, various modifications may be made without deviation from the spirit and scope of the invention. In one embodiment, various portions of the splice variant technique can be implemented with or assisted by a computer system. For example, the identification of in-frame exon-exon junctions can be performed by a computer system as can applying of mathematical algorithms to find a solution to the linear equations of the expression levels or to identify the spanning nucleotides based on molecular weights. Also, the searching of various databases can be performed by a computer system as well as the trimming and extending of exons. The computer system may include a central processing unit ("CPU"), main memory, secondary memory (e.g., disk drive), and input/output devices (e.g., display device and pointing device). The programs that implement the techniques may be stored in a computer-readable medium, such as a disk. Accordingly, the invention is not limited except by the following claims.

We claim:

1. A computer-implemented method for identifying expression levels of multiple expected polynucleotide splice variants of a gene in a sample, comprising:

obtaining expression level data from a microarray experiment for a plurality of indicator polynucleotides specific to exon-exon junctions of multiple expected splice variants of a gene; and applying a computer-implemented mathematical algorithm to the expression level data for the plurality of indicator polynucleotides to identify expression levels of each expected polynucleotide splice variant in the sample.

2. The method of claim 1 wherein the mathematical algorithm is a linear equation.

3. The method of claim 1 wherein the mathematical algorithm is a least-squares mathematical algorithm.

* * * * *